United States Patent [19]

Block et al.

[11] Patent Number: 5,593,870
[45] Date of Patent: Jan. 14, 1997

[54] PROCESS FOR PRODUCING FRENOLICIN B

[75] Inventors: David E. Block, Lawrenceville; Theron E. Hermann, Kinnelon; Jih-Han Hsieh, Parsippany; Nikhil S. Mehta, Livingston; Vishva R. Rai, Randolph, all of N.J.

[73] Assignee: Hoffmann-La Roche Inc., Nutley, N.J.

[21] Appl. No.: 305,625

[22] Filed: Sep. 14, 1994

[51] Int. Cl.$^6$ .................................................. C12P 17/18
[52] U.S. Cl. ........................ 435/119; 435/118; 435/117; 435/125; 435/127; 435/886
[58] Field of Search ................................. 435/119, 118, 435/125, 117, 127, 886

[56] References Cited

U.S. PATENT DOCUMENTS 4,199,514  4/1980  Omura et al. ........................ 435/886

OTHER PUBLICATIONS

Staubury et al., "Principles of Fermentation Technology", 1984, pp. 33–47.
Van Meter et al., Antimicrobial Agents Annual 1960, pp. 77–80, Gray et al., eds.. Plenum Press, New York 1961.
Iwai et al., J. of Antibiotics 31:959–965.
Belter et al., Bioseparations—Downstream Processing for Biotechnology, Wiley–Interscience Publications, pp. 17, 25, 99, 105, 109 (1988).

*Primary Examiner*—Irene Marx
*Attorney, Agent, or Firm*—George W. Johnston; Robert A. Silverman

[57] ABSTRACT

The present invention is directed to a process for producing frenolicin B. The process comprises fermenting a broth so as to produce frenolicin, said broth having a microorganism capable of producing frenolicin. The frenolicin is then converted in the broth under anaerobic conditions to deoxyfrenolicin. The deoxyfrenolicin is converted to frenolicin B.

5 Claims, 3 Drawing Sheets

PROCESS FOR PRODUCING FRENOLICIN B

BACKGROUND OF THE INVENTION

1. Field of the Invention

The invention relates to the production of antibiotic frenolicin B and its precursor deoxyfrenolicin.

2. Background

The biosynthesis of frenolicin, a compound of the structure

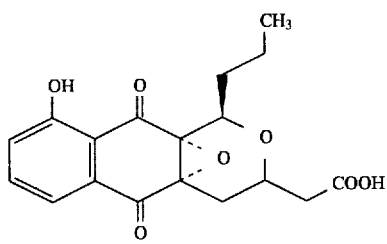

was first reported in *Antimicrob. Ag. Ann.*-1960, 77:1961. Frenolicin was produced by cultivation of a soil isolate identified as *Streptomyces fradiae* under conventional agitation and aeration conditions. Frenolicin displayed antibiotic activity.

It was later reported that frenolicin could be chemically converted to deoxyfrenolicin, a compound of the structure

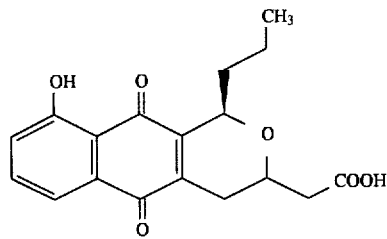

by reduction with any of a variety of agents. (*J,. Am. Chem. Soc.*, 88:4109, 1966; *J. Am. Chem. Soc.*, 90:1325, 1968; U.S. Pat. No. 3,452,051).

The biosynthesis of deoxyfrenolicin was first reported in U.S. Pat. No. 4,199,514 and *J. Antibiot.*, 31;959, 1978). These documents describe fermentation of a broth containing *Streptomyces roseofulvus* strain AM-3867 (ATCC No. 31476) carried out under aeration and aerobic conditions. Such fermentation produced a culture broth containing frenolicin, deoxyfrenolicin and an antibiotic frenolicin B having the chemical structure

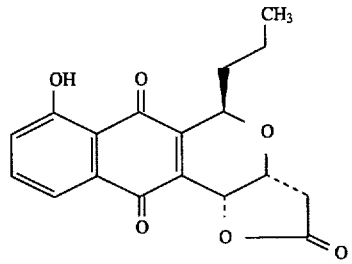

After completion of the fermentation, the culture broth is separated into the bacterial cells and the filtrate. The filtrate of a culture broth produced by fermentation of a Streptomyces microorganism can be treated by conventional methods, such as by treatment with pH or temperature. (See Belter et al., Bioseparations—Downstream Processing for Biotechnology, J. Wiley & Sons, New York 1988, pp. 17, 25, 99, 105). However, previous procedures to separate and recover the antibiotics after completion of the fermentation described in U.S. Pat. No. 4,199,514 and *J. Antibiot.*, 31:959, 1978 resulted in a recovery yield of frenolicin B of less than 50%.

BRIEF SUMMARY OF THE INVENTION

The present invention is directed to a process for producing frenolicin B. The process comprises fermenting a broth so as to produce frenolicin, said broth having a microorganism capable of producing frenolicin. The frenolicin is then converted in the broth under anaerobic conditions to deoxyfrenolicin. The deoxyfrenolicin is converted to frenolicin B during the recovery and purification steps.

Applicants have discovered that the absence of oxygen (anaerobic conditions) and the presence of bacterial cells (in the broth) during the conversion foster improved yield of frenolicin B over that obtained previously.

DETAILED DESCRIPTION OF THE INVENTION

Figure 1:
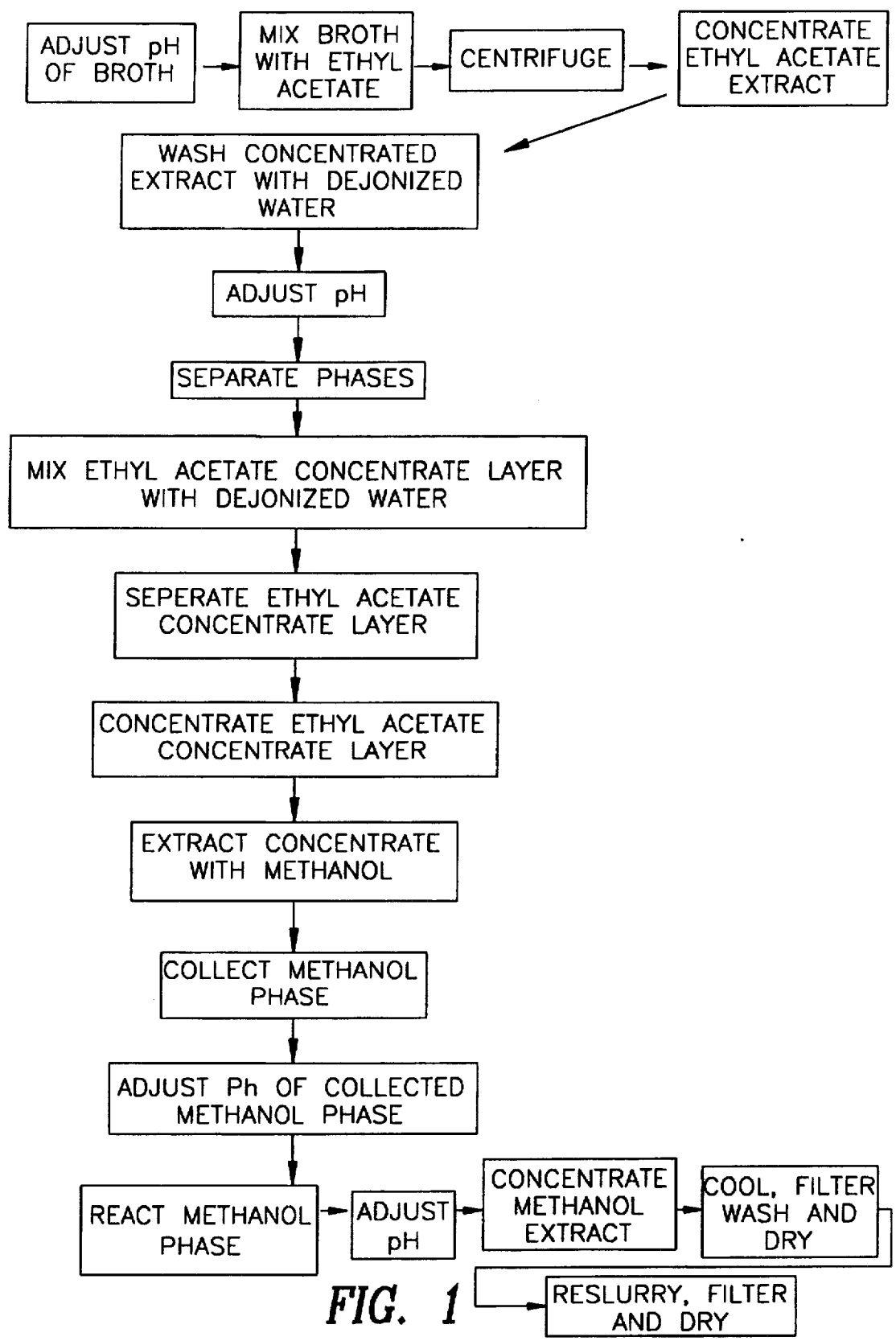
FIG. 1 is a flow chart of a process for production and recovery of frenolicin B.

The present invention is directed to a process for producing frenolicin B. The process comprises fermenting a broth so as to produce frenolicin, said broth having a microorganism capable of producing frenolicin. The frenolicin is then converted in the broth under anaerobic conditions to deoxyfrenolicin. The deoxyfrenolicin is converted to frenolicin B during the recovery and purification steps.

In the present invention, any microorganism may be used that is capable of producing the compound frenolicin. Preferred are mutant strains of *Streptomyces roseofulvus* obtained by subjecting *Streptomyces roseofulvus* to mutagenic treatment. A preferred mutant strain, *Streptomyces roseofulvus* AM-3867, its more specifically described in U.S. Pat. No. 4,199,514. The most preferred strain is *Streptomyces roseofulves* PF1-11, a mutant strain of *Streptomyces roseofulvus* AM-3867 deposited on Jul. 15, 1994 with the American Type Culture Collection, 12301 Parklawn Drive, Rockville, Md. U.S.A. 20852 and having deposite No. ATCC 55598. Other microorganisms which may be used in the invention include *Streptomyces fradiae* (*Antimicrob. Ag. Ann.*-1960, 77:1961) and the mutant strain of *Streptomyces roseofulvus* deposited with the American Type Culture Collection, Maryland, U.S.A. as ATCC No. 19921.

Fermentation is carried out in any conventional manner. For example, the microorganism is maintained as lyophilized stock or frozen in liquid nitrogen with 5% lactose and 10% glycerol. The lyophilized stock may be thawed and rehydrated with sterilized deionized water. The culture may be serially diluted and spread on agar slants and/or plates to grow and produce spores in an incubator. The spores are scraped off from the slants or plates to inoculate a seed medium in Erlenmeyer flasks or frozen in 5% lactose and 10% glycerol for later inoculations. The seed medium comprises, for example, starch, dextrose, Bacto tryprone, yeast extract, and calcium carbonate. After incubation of the inoculated seed medium, for example in a rotary shaker, the grown microorganism is inoculated into a production medium for fermentation. A typical production medium for use on the inventive process contains corn oil, dextrin, corn steep solids, cane molasses, sodium formate or citrate, yeast extract, soy flour, magnesium sulfate, monobasic sodium phosphate, calcium carbonate, and an antifoam agent such as polypropyleneglycol monobutyl ether.

The fermentation temperature is generally from about 25° C. to about 34° C. The fermentation is completed at a suitable time, when the titer (concentration) of frenolicin is judged to reach its maximum. The titer of frenolicin is judged to reach its maximum when the rate of production of frenolicin is no longer increasing over time. The titer of frenolicin may be determined, for example, by a HPLC assay method. A typical fermentation time is from about 160 to about 240 hours.

In the fermentation broth, there are formed and accumulated frenolicin and a small quantity of deoxyfrenolicin. Anaerobic treatment of the broth allows for in situ conversion of frenolicin to deoxyfrenolicin. Such treatment may comprise stripping the broth of oxygen with nitrogen. Upon stripping the broth of oxygen, the pH of the broth should be from about 7.0 to about 9.0, preferably from about 7.5 to about 8.4, and most preferably about 7.9. If necessary, the pH can be adjusted to about 7.9. The broth is then held under anaerobic conditions for from about 2 to about 8 hours, depending on the medium composition and frenolicin concentration. The pH of the broth may then be adjusted to from about 10 to about 11.5 and held for an additional 0.5 to 1 hour under anaerobic conditions.

The preferred process for production and recovery of frenolicin B is shown in FIG. 1.

After completion of the conversion, the deoxyfrenolicin is separated and collected from the fermentation broth. Preferably, the fermentation broth is adjusted to a pH of 2 to 5.5 and mixed with 0.5 to 2 volume of ethyl acetate at a pH of about 3. The whole fermentation broth and the ethyl acetate solvent mixture is centrifuged to obtain an ethyl acetate supernatant. The heavy bottom phase including the extracted broth, cells and solids is separated and discarded. The ethyl acetate extract is then concentrated to a deoxyfrenolicin concentration of 15 to 20 g/L.

The collected deoxyfrenolicin is further processed before conversion to frenolicin B in order to remove impurities. Preferably, the above ethyl acetate concentrate is washed with 0.3 to 1 volume of deionized water. The pH is adjusted to about 5.5 to 6.3, and the ethyl acetate concentrate/water mixture is mixed for 0.25 to 0.75 hour and allowed to settle for phase separation. The resulting ethyl acetate concentrate supernatant is separated and its pH adjusted to 2.8 to 3.5. The ethyl acetate concentrate layer is mixed with 0.12 to 0.17 volumes of deionized water to facilitate pH adjustment. The ethyl acetate concentrate layer containing the deoxyfrenolicin is separated from the water layer. The water washed ethyl acetate extract concentrate is then further concentrated to an oily paste or until no distillate comes off.

The deoxyfrenolicin is then converted to frenolicin B. The oily paste concentrate is extracted with 12 to 18 volumes of methanol, depending on the residual oil content in the harvested fermentation broth, to a deoxyfrenolicin concentration of from about 7 to about 12 g/L in the methanol extract. The upper methanol phase is collected, its pH adjusted to from about 6.0 to 6.2, and mixed for 0.2 to 0.5 hours. The methanol extract is then reacted for about 9 to about 16 hours at from about 36° C. to about 45° C. and at an air pressure of 5 to 10 psig. The reaction is quenched by adjusting the methanol extract pH to from about 2.8 to about 3.4.

The frenolicin B is then crystallized. The methanol extract is concentrated to a frenolicin B concentration of about 45 to about 60 g/L. The concentrated slurry is cooled at 0° C. to 4° C. for about 16 to about 24 hours. The slurry is filtered and the resulting wet cake is washed with an equal volume of cold (for example, about 4° C.) methanol having a pH of about 2 and is dried. The dried frenolicin B solids are reslurried in about 10 volumes of hexane for about 10 to about 15 minutes, the resulting slurry is filtered, and the resulting cake dried. The methanol mother liquor can be concentrated to recover a second crop of frenolicin B.

Figure 2:
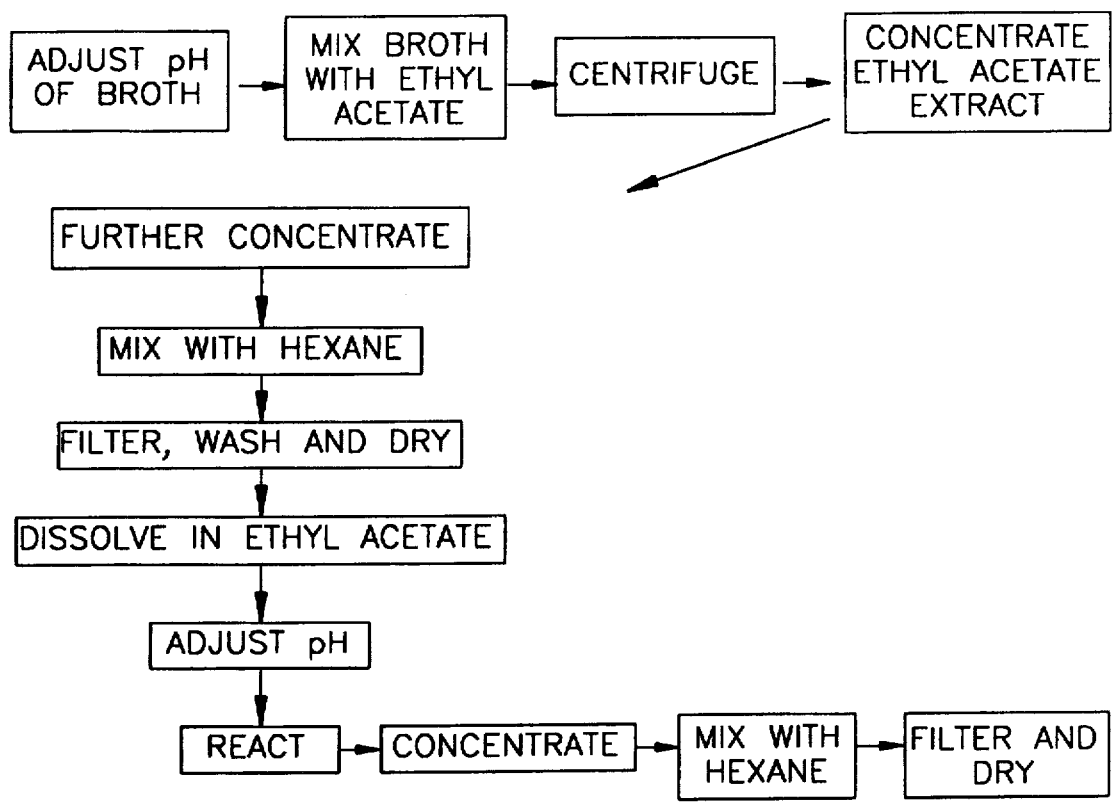
FIG. 2 is a flow chart of an alternative process for production and recovery of frenolicin B.

An alternative process for production and recovery of frenolicin B is shown in FIG. 2.

This alternative process for converting the deoxyfrenolicin to frenolicin B eliminates the water washing step and methanol extraction steps of the above described process. This process comprises further concentrating the ethyl acetate extract concentrate having a deoxyfrenolicin concentration of 15 to 20 g/L to an oily paste or until no distillate comes off the concentrate. The oily paste concentrate is mixed with 1 to 3 volumes of hexane for 0.25 to 0.5 hours to dissolve the oils. The deoxyfrenolicin hexane slurry is filtered, and the resulting cake is washed with 2 to 3 volumes of hexane and is dried. The solids are redissolved in ethyl acetate to a deoxyfrenolicin concentration of from about 30 to about 55 g/L. The pH of the ethyl acetate solution is adjusted to about from 5.9 to about 6.8. The ethyl acetate solution is reacted for from about 16 to about 36 hours at about 45° C. and at about 5 to about 10 psig air blanket to convert deoxyfrenolicin to frenolicin B. The converted frenolicin B in ethyl acetate is concentrated to a solvent free frenolicin B slurry. The slurry is mixed with about 1 to about 2 volumes of hexane and filtered and the resulting cake is dried.

Figure 3:
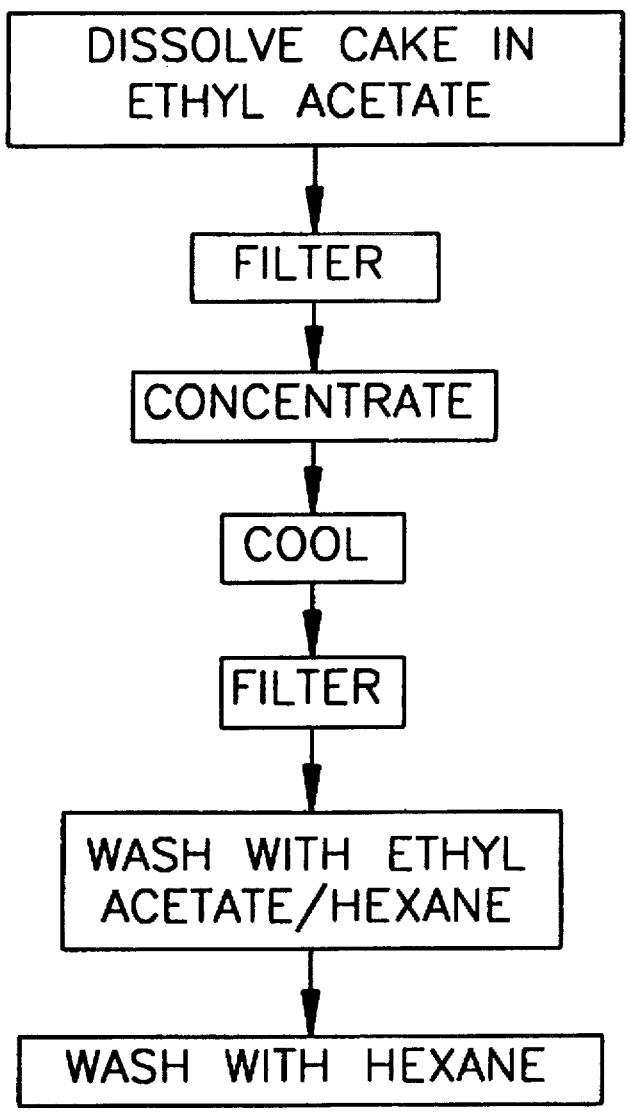
FIG. 3 is a flow chart of a process for purification of frenolicin B.

In either process, the dried cake is recrystallized as shown in FIG. 3. The dried cake is dissolved in ethyl acetate at ambient temperature to a concentration of from about 70 to about 100 g/L. The ethyl acetate solution is filtered and the filtrate is concentrated in nitrogen and under vacuum at 35° C. to a frenolicin B concentration of from about 275 to 350 g/L. The concentrate is cooled under filtered nitrogen blanket and the slurry filtered under cold (for example, 4° C.) conditions. The cake is washed with cold (for example, 4° C.) 50/50 v/v % ethyl acetate/hexane solution and then with hexane. The frenolicin B crystals are then dried.

The following examples are illustrative of the invention.

EXAMPLES

Determination of Frenolicins

The following HPLC assay method was used to analyze frenolicin, deoxyfrenolicin, and frenolicin B. A Hewlett Packard HPLC system including HP 1050 series variable wavelength detector, pumping systems and a HP 3396 series II integrator was used with a Waters HPLC column Nova-Pak C18 (3.9×150 mm) with a C18 Guard-PAKS precolumn. The column was operated at ambient temperatures (20° to 25° C.) and 1,800 psi pressure. The mobile phase solution was a mixture of 60% (v/v) 2% acetic acid and 40% (v/v) acetonitrile filtered through a 0.2 micron filter and deaerated with helium.

Fermentation broth samples were diluted (10×) with acidic methanol (1:500 HCl:methanol) and filtered (0.45 micron) before injection to the HPLC column. Samples taken during the recovery and purification process were diluted with appropriate volumes of methanol and filtered before the HPLC measurement. Samples were prepared in 2-mL vials, capped and automatically injected to the HPLC column at a draw speed of 350 micro L/min, with 20 micro L injection volume, at 1.2 mL/min flow rate and with detector wavelength at 276 nm. A calibration curve was prepared based on purified frenolicin compounds. The retention times for frenolicin, deoxyfrenolicin, and frenolicin B are 5.7, 8.1, and 11.6 min, and the detector response factors (g/L product concentration/peak area) are 3.40×10E-8, 8.47×10E-9, and 9.28×10E-9, respectively.

EXAMPLE 1

*Streptomyces roseofulvus* mutant strain deposited with the American Type Culture Colection, Maryland, U.S.A. as ATCC No. 55598 was used as the microorganism for fermentation. The spore stock, 5 mL aliquots frozen at −70° C. with 5% lactose and 10% glycerol, were thawed, serially diluted, and spread on agar plates containing 0.5 g/L yeast extract (Amberex 1003, Red Star, Universal Foods), 0.5 g/L asparagine (Sigma), 39 g/L potato dextrose agar (Difco), and agar 10 g/L (Difco), in deionized water to grow spores in the incubator at 27° C. for 7 days. The spores were scraped off from the plates using 5 g/L sterile agar solution. About $10^8$ spores were used to inoculate a 1 L seed medium in 6-L Erlenmeyer flasks. The seed medium contained, per L, 5 g yeast extract (Amberex 1003, Red Star, Universal Foods), 5 g Bacto tryptone (Difco), 10 g glucose, 20 g corn starch (Eclipse N, Staley), and 4 g $CaCO_3$ (Whittaker Clark Daniels) in deionized water. The flasks were incubated at 27° C. in a rotary shaker operating at 220 RPM for 48 hours. 0.8 L of the grown microorganisms in the seed medium was used to inoculate 40 L fermentation batch. 60 L seed inoculum was used to inoculate a 2,000-L fermentation with 1,325 L working volume of fermentation broth. The broth (1,325 L) contains initially, per L, 50 g corn oil (Welch, Holme and Clark), 20 g dextrin (Sigma type IV), 15 g corn steep solids (Roquette), 10 g cane molasses (Mid-Eastern), 7.5 g sodium formate (Fisher), 3 g yeast extract (Amberex 1003), 4 g $MgSO_4 \cdot 7H_2O$ (Fisher), 0.44 g $NaH_2PO_4 \cdot 7H_2O$ (Fisher), 4 g $CaCO_3$ (Pfizer), and 0.3 mL of an antifoam agent (Union Carbide, UCON® LB-625, polypropylene glycol monobutyl ether).

The fermentation was conducted at 27° C., 5 psig back pressure, dissolved oxygen maintained above 30% by controlling the agitation between 160 and 280 RPM, and by controlling the aeration between 336 and 672 L/min. The pH of the fermentation broth was not controlled and measured between 6.5 and 8.4.

After the completion of fermentation (186 hours, 1,325 L, pH 8.2, frenolicin 3.8 g/L, deoxyfrenolicin, 0.1 g/L), the aeration in the fermentor (2,000-L) was turned off and the fermentation broth was stripped with nitrogen to remove oxygen. The fermentor agitation was reduced from 280 to 100 RPM.

The fermentation broth temperature was reduced from 27° C. to 10° C. with chilled water and held for 7 hours to convert frenolicin to deoxyfrenolicin. The converted broth (1,325 L, pH 7.7, frenolicin 0.2 g/L, deoxyfrenolicin 2.9 g/L) was adjusted to pH 11.5 using 12.9 L 50% NaOH and mixed for 30 minutes under nitrogen. The broth pH was then adjusted to 2.5 using 14 L concentrated $H_2SO_4$ and immediately extracted with ethyl acetate (1,325 L) for 30 min.

The whole fermentation broth and the ethyl acetate extract mixture was centrifuged in a Westfalia disk type separator (Model SA-7-06-076) at 280 L/hr flow rate. The separated ethyl acetate extract (light phase, 1,298 L, pH 2.7, frenolicin 0.12 g/L, deoxyfrenolicin 2.91 g/l) was concentrated in a wiped-film evaporator (Artisan, BD410, EVP-122) at 50° C., 28" vacuum, and 52 L/hr feed flow rate. The ethyl acetate extract concentrate (190 L, pH 3.0, deoxyfrenolicin 19.5 g/L, frenolicin 0.83 g/L) was washed with 93 L of deionized water, adjusted to pH 6.1 with concentrated $NH_4OH$, and mixed for 30 min. The washed ethyl acetate concentrate was separated by phase separation, mixed with 32 L deionized water, and adjusted to pH 3 with concentrated HCl.

The separated and water washed ethyl acetate extract concentrate layer (224 L, pH 3, deoxyfrenolicin 16.3 g/L) was further concentrated in a rotary evaporator (50-L, 30-L capacity, Buchi Rotavapor Model 185 Ex, EVP-454) at 40° C. and 28" vacuum to an oily paste. The oily paste (28 L) was extracted with 430 L of methanol. The separated upper phase methanol extract (426 L, pH 3.2, deoxyfrenolicin 8.28 g/L) was adjusted to pH 6.1 with 1M $NH_4OH$. The pH adjusted methanol extract was reacted at 38° C. under 10 psig air for 12 hours to convert deoxyfrenolicin to frenolicin B. The reaction was quenched by adjusting the methanol extract to pH 3.0 with 1M HCl.

The quenched methanol extract (426 L, frenolicin B 7.35 g/L, deoxyfrenolicin 0.2 g/L) was concentrated in the wiped-film evaporator at 45° C., 28" vacuum, and 20 L/hr feed flow rate. The concentrated methanol extract slurry (66 L, frenolicin B 46.4 g/L) was cooled at 0° C overnight to crystallize frenolicin B and filtered (Whatman No. 1 filter). The wet frenolicin B cake was washed with cold pH 2 methanol and vacuum (25") dried (30° C.) overnight. The dried crude frenolicin B solids were reslurried in hexane (37 L) to remove oils and filtered. The hexane washed solids were vacuum dried to obtain 3,060 g frenolicin B with 90% purity.

The 90% purity frenolicin B was further purified by dissolving the frenolicin B solids in ethyl acetate to a concentration of 80 g/L. The frenolicin B ethyl acetate solution was filtered (Whatman No. 1 filter) and concentrated under nitrogen and 25" vacuum at 35° C. in a crystallizer to a frenollicin B concentration of 300 g/L. The concentrate was cooled at a programmed rate of 2.1° C./hr for 16 hrs to 0° C. The crystallized frenolicin B was filtered, washed with cold (4° C.) 50/50 (v/v) % ethyl acetate and hexane, and dried under vacuum to obtain 2,640 g frenolicin B with 98.5% purity.

EXAMPLE 2

The *Streptomyces roseofulvus* seed inoculum preparation, mycelial fermentation, frenolicin conversion to deoxyfrenolicin in the fermentation broth, whole broth extraction with ethyl acetate, centrifugation, and ethyl acetate extract concentration procedures are the same as those described in Example 1. The ethyl acetate extract concentrate (26 L, deoxyfrenolicin 19.8 g/L, frenolicin 1.4 g/L) was further concentrated in a rotary evaporator at 40° C. and 28" vacuum to distill off residual ethyl acetate to an oily paste. To the oily paste (12 L, deoxyfrenolicin 42 g/L) was added 18 L hexane and mixed for 0.5 hrs to dissolve the oils. The deoxyfrenolicin hexane slurry was filtered under 25" vacuum with Whatman filter paper. The crude deoxyfrenolicin cake (816 g, 56% purity) was washed with 3 L hexane and dried in a vacuum (25") oven at 30° C. overnight. The combined filtrate and hexane wash (32 L, deoxyfrenolicin 1.4 g/L) can be concentrated and recycled.

The filtered and dried crude deoxyfrenolicin solids (816 g, 56% purity) were redissolved in ethyl acetate (10 L) to a deoxyfrenolicin concentration of 45 g/L. The pH of the deoxyfrenolicin in ethyl acetate solution was adjusted to pH 6.1 with $NH_4OH$. The solution was heated to 45° C. with mixing and ethyl acetate reflux, and the mixing vessel was blanketed with 5 to 10 psig air. The pH of solution during the reaction was maintained at pH 5.9 to 6.1 with addition of $NH_4O$ H. Deoxyfrenolicin was converted to frenolicin B with 92% conversion in 24 hrs. The converted frenolicin B in ethyl acetate solution (9.5 L, frenolicin B 43 g/L) was concentrated in the rotary evaporator at 40° C. and 28" vacuum to evaporate ethyl acetate. The solvent free crude frenolicin B solid slurry (1.2 L) was mixed with 2.4 L hexane and filtered under 25" vacuum with Whatman filter paper, washed with hexane and vacuum (25") oven dried at 30° C. overnight. The frenolicin B solid (445 g, 87% purity) can be further purified with the recrystallization procedures as those described in Example 1.

It is claimed:

1. A process for producing deoxyfrenolicin which comprises:
    (a) culturing under aerobic conditions in an aqueous culture medium containing assimilable sources of carbon and nitrogen and inorganic substances the strain of *Streptomyces roseofulvus* deposited with the American Type Culture Collection as ATCC No. 55598 or a mutant thereof which is capable of producing frenolicin, so as to produce frenolicin;
    (b) then continuing the culturing under anaerobic conditions to cause a conversion of frenolicin to deoxyfrenolicin under anaerobic conditions; and
    (c) recovering deoxyfrenolicin produced,
wherein the anaerobic conditions are created at about the point in time when the titer of frenolicin is at its maximum.

2. The process of claim 1, further comprising retaining anaerobic conditions for from about 2 to about 8 hours at a pH of from about 7.0 to about 9.0.

3. The process of claim 2, wherein the pH is from about 7.5 to about 8.4.

4. The process of claim 2, wherein the pH is about 7.9.

5. A process for producing frenolicin B which comprises:
    (a) culturing under aerobic conditions in an aqueous culture medium containing assimilable sources of carbon and nitrogen and inorganic substances the strain of *Streptomyces roseofulvus* deposited with the American Type Culture Collection as ATCC No. 55598 or a mutant thereof which is capable of producing frenolicin, so as to produce frenolicin;
    (b) then continuing the culturing under anaerobic conditions to cause a conversion of frenoliin to deoxyfrenolicin under anaerobic conditions;
    (c) recovering deoxyfrenolicin;
    (d) converting deoxyfrenolicin to frenolicin B by a chemical process; and
    (e) recovering frenolicin B,
wherein the anaerobic conditions are created at about the point in time when the titer of frenolicin is at its maximum.

* * * * *